US009238638B2

(12) United States Patent
Mignani et al.

(10) Patent No.: US 9,238,638 B2
(45) Date of Patent: Jan. 19, 2016

(54) METHOD FOR PREPARING ALCOHOL CARBONATE USING RARE EARTH OXIDES AS CATALYSTS

(75) Inventors: Gerard Mignani, Lyons (FR); Marc Lemaire, Villeurbanne (FR); Eric Da Silva, Lyons (FR); Wissam Dayoub, Villeurbanne (FR); Yann Raoul, Crezancy (FR)

(73) Assignees: RHODIA OPERATIONS, Aubervilliers (FR); CENTRE NATIONAL DE LA RECHERCHE SCIENTIFIQUE (C.N.R.S.), Paris (FR); UNIVERSITE CLAUDE BERNARD LYON 1, Villeurbanne (FR); FIDOP (FONDS DE DEVELOPPEMENT DES FILIERES DES OLEAGINEUX ET DES PROTEAGINEUX), Paris (FR)

( * ) Notice: Subject to any disclaimer, the term of this patent is extended or adjusted under 35 U.S.C. 154(b) by 0 days.

(21) Appl. No.: 13/978,459

(22) PCT Filed: Jan. 11, 2012

(86) PCT No.: PCT/EP2012/050326
§ 371 (c)(1),
(2), (4) Date: Sep. 11, 2013

(87) PCT Pub. No.: WO2012/095435
PCT Pub. Date: Jul. 19, 2012

(65) Prior Publication Data
US 2013/0345441 A1 Dec. 26, 2013

(30) Foreign Application Priority Data

Jan. 11, 2011 (FR) ...................... 11 50215

(51) Int. Cl.
*C07D 317/36* (2006.01)
*C07D 317/34* (2006.01)
(52) U.S. Cl.
CPC ............ *C07D 317/36* (2013.01); *C07D 317/34* (2013.01)
(58) Field of Classification Search
CPC ............................ C07D 317/34; C07D 317/36
See application file for complete search history.

(56) References Cited

U.S. PATENT DOCUMENTS

| 5,430,170 | A | * | 7/1995 | Urano et al. ................. 558/277 |
| 6,025,504 | A | | 2/2000 | Claude et al. |
| 6,506,705 | B2 | | 1/2003 | Blanchard et al. |
| 6,768,020 | B2 | * | 7/2004 | De Jonge et al. ............ 558/277 |
| 2010/0209979 | A1 | | 8/2010 | Jung et al. |
| 2011/0201828 | A1 | * | 8/2011 | Prochazka et al. ........... 549/229 |

FOREIGN PATENT DOCUMENTS

| CN | 101 822 992 A | | 9/2010 |
| CN | 101822992 A | * | 9/2010 |
| EP | 0 739 888 A1 | | 10/1996 |
| EP | 0 955 298 A1 | | 11/1999 |
| EP | 1 156 042 A1 | | 11/2001 |
| IN | 2009 MU 01574 A | | 4/2010 |
| JP | 6 329663 A | | 11/1994 |
| JP | 2008/001659 A | | 1/2008 |
| WO | 98/24726 A1 | | 6/1998 |
| WO | 2010/043581 A1 | | 4/2010 |
| WO | WO 2010/043581 | * | 4/2010 |

OTHER PUBLICATIONS

Tomishige et al. (Green Chem., 2004, 6, p. 206-214).*
Bai et al. (CN101822992 (A)—PD: Sep. 8, 2010—Machine Translation—p. 1-6).*
Veldurthy B et al.: "An efficient synthesis of organic carbonates: Atom economic protocol with a new catalytic system" Chemical Communications 20040321 GB, No. 6. Mar. 21, 2004. pp. 734-735. XP002636595, ISSN: 1359-7345 p. 735; examples 1, 3; table 3 p. 735. last paragraph.
Climent M J et al.: "Chemicals from biomass: Synthesis of glycerol carbonate by transesterification and carbonylation with urea with hydrotalcite catalysts. The role of acid-base pairs", Journal of Catalysis, Academic Press, Duluth, MN, US, vol. 269, No, I, Jan. 1, 2010, pp. 140-149, XP026815774, ISSN: 0021-9517 [retrieved on Dec. 5, 2009] abstract tables 2-6.
Manabu Hatano et al.: "Lanthanum(III) Isopropoxide Catalyzed Chemoselective Transesterification of Dimethyl Carbonate and Methyl Carbamates", Organic Letters, vol. 13, No. 3, Dec. 22, 2010, pp. 430-433, XP55018738, ISSN: 1523-7060, DOI: 10.1021/ol102754y abstract Scheme 1 and 2, p. 431-432.
International Search Report, dated Feb. 14, 2012, from corresponding PCT application.

* cited by examiner

*Primary Examiner* — Valerie Rodriguez-Garcia
(74) *Attorney, Agent, or Firm* — Young & Thompson

(57) ABSTRACT

Disclosed is a method for preparing, by transcarbonation, a compound of formula (I), including reacting a polyol of formula (II) with an alkyl carbonate or an alkylene carbonate in the presence of a catalytic system consisting of a catalytic entity selected from among the rare earth oxides or the mixtures thereof, and optionally an inert substrate.

18 Claims, No Drawings

METHOD FOR PREPARING ALCOHOL CARBONATE USING RARE EARTH OXIDES AS CATALYSTS

FIELD OF THE INVENTION

The present invention relates to a process for the synthesis of alcohol carbonate, in particular of glycerol carbonate.

BACKGROUND OF THE INVENTION

Processes for the synthesis of glycerol carbonate are widely described in the literature.

Processes employing organic carbonates have been developed.

EP 0 739 888 discloses in particular a process for the preparation of glycerol carbonate by reaction of glycerol and a cyclic organic carbonate in the presence of a solid catalyst comprising a bicarbonate-comprising or hydroxyl-comprising anionic macroporous resin or a three-dimensional zeolite of X or Y type comprising basic sites, at a temperature of between 50 and 110° C. The reaction yield is of the order of 90%. However, in order to obtain this yield, it is necessary to withdraw the ethylene glycol formed during the reaction. The process is applicable to pure glycerol and to glycerins.

It is also known from US2010/0209979 (Jung et al.) a process for the preparation of glycerol carbonate by reaction between dimethyl carbonate and glycerol by transesterification catalyzed by a lipase.

JP06329663 discloses a process for the preparation of glycerol carbonate by reaction between ethylene carbonate and glycerol catalyzed by aluminum, magnesium, zinc, titanium or lead oxides. Other processes have been developed by catalysis with CaO.

However, these catalysts are not stable and are in particular decomposed by water and do not make it possible to be able to carry out the process continuously.

There are other processes using in particular phosgene and urea. However, the process with phosgene exhibits the disadvantage of being highly toxic and thus not suitable for the preparation of products involved in the manufacture of food, cosmetic or pharmaceutical compositions.

Thus, EP 0 955 298 discloses a process for the synthesis of glycerol carbonate consisting of the reaction of glycerol with urea in the presence of a catalyst of metal or organometallic salt type exhibiting Lewis acid sites. The molar yield obtained is between 40 and 80% with respect to the glycerol.

However, the processes with urea generate a high proportion of ammonia; it is thus necessary to neutralize this ammonia in the salt form and these ammonia salts are not of economic value. Disadvantages in terms of cost, of difficulty in purification and sometimes of environmental (in particular discharge of dioxane and/or glycidol, use of glycidol, use of tin-based catalyst, use of acetonitrile) are also described.

The catalysts of the prior state of the art generally comprise a basic entity, in particular of metal oxide type. This basic entity is soluble in the presence of water or hydratable (undergoes a reaction with water), which damages its effectiveness. It is thus important to control the reaction medium, in particular the amount of water, in order to employ such catalysts.

There is thus a need to provide a process which can be easily operated industrially, which can be employed continuously and which does not exhibit a risk, in particular in terms of toxicity. There is also a need to provide a process which can be carried out in a reaction medium comprising water.

SUMMARY OF THE INVENTION

The present invention relates to a process for the preparation by transcarbonation of a compound of formula (I),

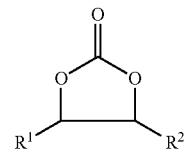

in which:
$R^1$ represents:
  a hydrogen atom;
  a linear, branched or cyclic $C_1$ to $C_9$, preferably $C_1$ to $C_5$, hydrocarbon group which can comprise one or more heteroatoms chosen in particular from oxygen, nitrogen or sulfur and which can comprise one or more OH substituents;
  a group of formula —$CH_2$—$R^3$ in which $R^3$ represents a linear or branched $C_1$ to $C_9$, preferably $C_1$ to $C_5$, hydrocarbon group which can comprise one or more heteroatoms chosen in particular from oxygen, nitrogen or sulfur and which can comprise one or more OH substituents;
  an alkyl-aryl group of formula -$Q^1$-$Ar^1$ in which $Q^1$ represents a $C_1$ to $C_9$, preferably $C_1$ to $C_5$, alkyl residue and $Ar^1$ represents a $C_6$ to $C_{14}$, preferably $C_6$, aryl group, which is optionally substituted;
  a $C_5$ to $C_{14}$, preferably $C_6$ to $C_{14}$, preferably $C_6$ to $C_{10}$, aryl group, which is optionally substituted, in particular by a $C_1$ to $C_9$, preferably $C_1$ to $C_5$, alkyl group; an optionally substituted $C_5$ to $C_{14}$, preferably $C_6$ to $C_{14}$, preferably $C_6$ to $C_{10}$, aryl group; an alkyl-aryl group of formula -$Q^2$-$Ar^2$ in which $Q^2$ represents a $C_1$ to $C_9$, preferably $C_1$ to $C_5$, alkyl residue and $Ar^2$ represents a $C_6$ to $C_{14}$, preferably $C_6$, aryl group which is optionally substituted; a polyalkoxy group of formula —($OCH_2CH_2$)$_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_9$, preferably $C_1$ to $C_5$, alkoxy group; or
  a heteroaryl group which preferably comprises from 5 to 10 members and which is optionally substituted, in particular by: a $C_1$ to $C_9$, preferably $C_1$ to $C_5$, alkyl group; an optionally substituted $C_5$ to $C_{14}$, preferably $C_6$ to $C_{14}$, preferably $C_6$ to $C_{10}$, aryl group; an alkyl-aryl group of formula -$Q^3$-$Ar^3$ in which $Q^3$ represents a $C_1$ to $C_9$, preferably $C_1$ to $C_5$, alkyl residue and $Ar^3$ represents a $C_6$ to $C_{14}$, preferably $C_6$, aryl radical which is optionally substituted; a polyalkoxy group of formula —($OCH_2CH_2$)$_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_9$, preferably $C_1$ to $C_5$, alkoxy group;
$R^2$ represents:
  a hydrogen atom;
  a linear or branched $C_1$ to $C_{10}$, preferably $C_1$ to $C_5$, alkyl group;
  a group of formula -$L^1$OH in which $L^1$ represents:
    a linear, branched or cyclic $C_1$ to $C_9$, preferably $C_1$ to $C_5$, hydrocarbon group which can comprise one or more heteroatoms chosen in particular from oxygen, nitrogen or sulfur and which can comprise one or more OH substituents;
    an alkyl-aryl group of formula -$Q^4$-$Ar^4$ in which $Q^4$ represents a $C_1$ to $C_9$, preferably $C_1$ to $C_5$, alkyl residue and $Ar^4$ represents a $C_6$ to $C_{14}$, preferably $C_6$, aryl group which is optionally substituted;

a group of formula -L²-CH₂ in which L² represents:
  a linear, branched or cyclic $C_1$ to $C_9$, preferably $C_1$ to $C_5$, hydrocarbon group which can comprise one or more heteroatoms chosen in particular from oxygen, nitrogen or sulfur and which can comprise one or more pendant OH groups;
  a $C_5$ to $C_{14}$, preferably $C_6$ to $C_{14}$, preferably $C_6$ to $C_{10}$, aryl group which is optionally substituted, in particular by a $C_1$ to $C_9$, preferably $C_1$ to $C_5$, alkyl group; an optionally substituted $C_5$ to $C_{14}$, preferably $C_6$ to $C_{14}$, preferably $C_6$ to $C_{10}$, aryl group; an alkyl-aryl group of formula -$Q^5$-$Ar^5$ in which $Q^5$ represents a $C_1$ to $C_9$, preferably $C_1$ to $C_5$, alkyl residue and $Ar^5$ represents a $C_6$ to $C_{14}$, preferably $C_6$, aryl group which is optionally substituted; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_9$, preferably $C_1$ to $C_5$, alkoxy group; or
  a heteroaryl group which is optionally substituted, in particular by: a $C_1$ to $C_9$, preferably $C_1$ to $C_5$, alkyl group; an optionally substituted $C_5$ to $C_{14}$, preferably $C_6$ to $C_{14}$, preferably $C_6$ to $C_{10}$, aryl group; an alkyl-aryl group of formula -$Q^6$-$Ar^6$ in which $Q^6$ represents a $C_1$ to $C_9$, preferably $C_1$ to $C_5$, alkyl residue and $Ar^6$ represents a $C_6$ to $C_{14}$, preferably $C_6$, aryl group which is optionally substituted; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_9$, preferably $C_1$ to $C_5$, alkoxy group;
a $C_5$ to $C_{14}$, preferably $C_6$ to $C_{14}$, preferably $C_6$ to $C_{10}$, aryl group which is optionally substituted, in particular by: a $C_1$ to $C_9$, preferably $C_1$ to $C_5$, alkyl group; an optionally substituted $C_5$ to $C_{14}$, preferably $C_6$ to $C_{14}$, preferably $C_6$ to $C_{10}$, aryl group; an alkyl-aryl group of formula -$Q^5$-$Ar^5$ in which $Q^5$ represents a $C_1$ to $C_9$, preferably $C_1$ to $C_5$, alkyl residue and $Ar^5$ represents a $C_6$ to $C_{14}$, preferably $C_6$, aryl group which is optionally substituted; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_9$, preferably $C_1$ to $C_5$, alkoxy group; or
a heteroaryl group which preferably comprises from 5 to 10 members and which is optionally substituted, in particular by: a $C_1$ to $C_9$, preferably $C_1$ to $C_5$, alkyl group; an optionally substituted $C_5$ to $C_{14}$, preferably $C_6$ to $C_{14}$, preferably $C_6$ to $C_{10}$, aryl group; an alkyl-aryl group of formula -$Q^6$-$Ar^6$ in which $Q^6$ represents a $C_1$ to $C_9$, preferably $C_1$ to $C_5$, alkyl residue and $Ar^6$ represents a $C_6$ to $C_{14}$, preferably $C_6$, aryl group which is optionally substituted; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_9$, preferably $C_1$ to $C_5$, alkoxy group;

comprising the reaction, in the presence of a catalytic system composed of a catalytic entity chosen from rare earth metal oxides or mixtures of rare earth metal oxides and optionally of an inert support, between a polyol of formula (II)

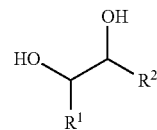

(II)

and an alkyl carbonate or an alkylene carbonate.

DETAILED DESCRIPTION OF THE INVENTION

Preferably, in the process of the invention, $R^1$ represents:
a hydrogen atom;
a linear or branched $C_1$ to $C_9$, preferably $C_1$ to $C_4$, alkyl group which can comprise one or more heteroatoms chosen in particular from oxygen, nitrogen or sulfur and which can comprise one or more OH substituents; preferably methylene or ethylene;
a group of formula —$CH_2$—$R^3$ in which $R^3$ represents a linear or branched $C_1$ to $C_9$, preferably $C_1$ to $C_5$, alkyl group which can comprise one or more heteroatoms chosen in particular from oxygen, nitrogen or sulfur and which can comprise one or more OH substituents; preferably methylene or ethylene;
an alkyl-aryl group of formula -$Q^1$-$Ar^1$ in which $Q^1$ represents a $C_1$ to $C_9$, preferably $C_1$ to $C_5$, alkyl residue and $Ar^1$ represents a phenyl group which is optionally substituted; for example methylphenyl or ethylphenyl;
a phenyl group which is optionally substituted, in particular by: a $C_1$ to $C_9$, preferably $C_1$ to $C_5$, alkyl group, for example methyl or ethyl; an optionally substituted phenyl group; an alkyl-aryl group of formula -$Q^2$-$Ar^2$ in which $Q^2$ represents a $C_1$ to $C_9$, preferably $C_1$ to $C_5$, alkyl residue and $Ar^2$ represents an optionally substituted phenyl group, for example methylphenyl or ethylphenyl; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_5$ alkoxy group, for example methoxy or ethoxy;
a $C_5$ to $C_6$ cycloalkyl group which is optionally substituted, in particular by a $C_1$ to $C_5$ alkyl group, for example methyl or ethyl; an optionally substituted phenyl group; an alkyl-aryl group of formula -$Q^7$-$Ar^7$ in which $Q^7$ represents a $C_1$ to $C_9$, preferably $C_1$ to $C_5$, alkyl residue and $Ar^7$ represents an optionally substituted phenyl group, preferably methylphenyl or ethylphenyl; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_5$ alkoxy group, for example methoxy or ethoxy; or
a heteroaryl group of pyridinyl or thiophenyl type which is optionally substituted, in particular by a $C_1$ to $C_5$ alkyl group, for example methyl or ethyl; an optionally substituted phenyl group; an alkyl-aryl group of formula -$Q^3$-$Ar^3$ in which $Q^3$ represents a $C_1$ to $C_9$, preferably $C_1$ to $C_5$, alkyl residue and $Ar^3$ represents an optionally substituted phenyl group, for example methylphenyl or ethylphenyl; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_5$ alkoxy group, for example methoxy or ethoxy.

Preferably, in the process of the invention, $R^2$ represents:
a hydrogen atom;
a linear or branched $C_1$ to $C_9$, preferably $C_1$ to $C_5$, alkyl group, for example methyl, ethyl or propyl;
a group of formula -$L^1$OH in which $L^1$ represents:
- a linear or branched $C_1$ to $C_9$, preferably $C_1$ to $C_5$, alkyl group which can comprise one or more heteroatoms chosen in particular from oxygen, nitrogen or sulfur and which can comprise one or more OH substituents, for example methylene or ethylene;
- an alkyl-aryl group of formula -$Q^4$-$Ar^4$ in which $Q^4$ represents a $C_1$ to $C_9$, preferably $C_1$ to $C_5$, alkyl residue and $Ar^4$ represents a phenyl group which is optionally substituted, preferably methylphenyl or ethylphenyl;

a group of formula -$L^2$-$CH_2$ in which $L^2$ represents:
- a linear or branched $C_1$ to $C_9$, preferably $C_1$ to $C_5$, alkyl group which can comprise one or more heteroatoms chosen in particular from oxygen, nitrogen or sulfur and which can comprise one or more pendant OH groups;
- a phenyl group which is optionally substituted, in particular by a $C_1$ to $C_5$ alkyl group, for example methyl or ethyl; an optionally substituted phenyl group; an alkyl-aryl group of formula -$Q^5$-$Ar^5$ in which $Q^5$ represents a $C_1$ to $C_9$, preferably $C_1$ to $C_5$, alkyl residue and $Ar^5$ represents an optionally substituted phenyl group, preferably methylphenyl or ethylphenyl; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_5$ alkoxy group, for example methoxy or ethoxy;
- a $C_5$ to $C_6$ cycloalkyl group which is optionally substituted, in particular by a $C_1$ to $C_5$ alkyl group, for example methyl or ethyl; an optionally substituted phenyl group; an alkyl-aryl group of formula -$Q^8$-$Ar^8$ in which $Q^8$ represents a $C_1$ to $C_9$, preferably $C_1$ to $C_5$, alkyl residue and $Ar^8$ represents an optionally substituted phenyl group, preferably methylphenyl or ethylphenyl; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_5$ alkoxy group, for example methoxy or ethoxy;
- a heteroaryl group of thiophenyl or pyridinyl type which is optionally substituted, in particular by a $C_1$ to $C_5$ alkyl group, for example methyl or ethyl; an optionally substituted phenyl group; an alkyl-aryl group of formula -$Q^6$-$Ar^6$ in which $Q^6$ represents a $C_1$ to $C_9$, preferably $C_1$ to $C_5$, alkyl residue and $Ar^6$ represents an optionally substituted phenyl group, preferably methylphenyl or ethylphenyl; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_5$ alkoxy group, for example methoxy or ethoxy;

a $C_5$ to $C_6$ cycloalkyl group which is optionally substituted, in particular by a $C_1$ to $C_5$ alkyl group, for example methyl or ethyl; an optionally substituted phenyl group; an alkyl-aryl group of formula -$Q^8$-$Ar^8$ in which $Q^8$ represents a $C_1$ to $C_9$, preferably $C_1$ to $C_5$, alkyl residue and $Ar^8$ represents an optionally substituted phenyl group, preferably methylphenyl or ethylphenyl; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_5$ alkoxy group, for example methoxy or ethoxy; or a heteroaryl group of thiophenyl or pyridinyl type which is optionally substituted, in particular by a $C_1$ to $C_5$ alkyl group, for example methyl or ethyl; an optionally substituted phenyl group; an alkyl-aryl group of formula -$Q^6$-$Ar^6$ in which $Q^6$ represents a $C_1$ to $C_9$, preferably $C_1$ to $C_5$, alkyl residue and $Ar^6$ represents an optionally substituted phenyl group, preferably methylphenyl or ethylphenyl; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_5$ alkoxy group, for example methoxy or ethoxy.

In the context of the present invention, the expression "between x and y" is also understood to cover the limits x and y. Thus, "between x and y" can be understood, in the context of the invention, as meaning "ranging from x to y".

For example, the polyol can be chosen from ethylene glycol, propylene glycol, glycerol, erythritol or sorbitol and the compound of formula (I) is the corresponding compound.

Preferably, in the process of the invention, $R^2$ represents a group of formula -$L^1$ OH.

Advantageously, the compound of formula (I) is a compound of formula (Ia)

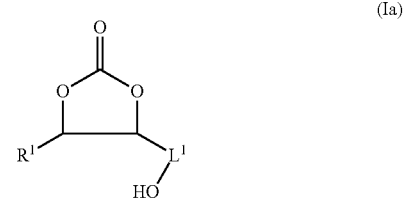

(Ia)

and the polyol of formula (II) is a polyol of formula (IIa)

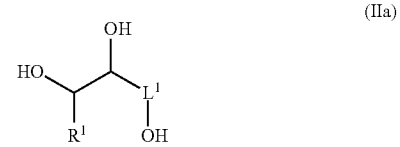

(IIa)

in which $R^1$ and $L^1$ have the above mentioned definitions.

In a specific embodiment, $L^1$ is a linear or branched alkyl radical comprising at least one —OH substituent.

In a specific embodiment, the polyol is a polyglycerol.

Advantageously, the compound of formula (I) is glycerol carbonate, having the following formula

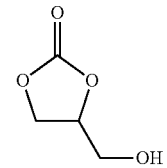

and the polyol is glycerol.

In the process according to the invention, the alkyl carbonate can be a compound of formula (III)

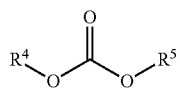

(III)

in which $R^4$ and $R^5$, which are identical or different, represent:
- a linear or branched $C_1$ to $C_{20}$ alkyl group;
- a $C_5$ to $C_{14}$, preferably $C_6$ to $C_{14}$, aryl group which is optionally substituted, in particular by a $C_1$ to $C_9$, preferably $C_1$ to $C_5$, alkyl group; an optionally substituted $C_6$ to $C_{14}$, preferably $C_6$ to $C_{14}$, preferably $C_6$ to $C_{10}$, aryl group; an alkyl-aryl group of formula $-Q^9-Ar^9$ in which $Q^9$ represents a $C_1$ to $C_9$, preferably $C_1$ to $C_6$, alkyl residue and $Ar^9$ represents a $C_6$ to $C_{14}$, preferably $C_6$, aryl group which is optionally substituted; a polyalkoxy group of formula $-(OCH_2CH_2)_n-OR^{15}$ in which n represents an integer between 2 and 5 and $R^{15}$ represents a $C_1$ to $C_{10}$, preferably $C_1$ to $C_5$, alkyl group; or a $C_1$ to $C_9$, preferably $C_1$ to $C_5$, alkoxy group;
- a $C_5$ to $C_6$ cycloalkyl group which is optionally substituted, in particular by a $C_1$ to $C_9$, preferably $C_1$ to $C_5$, alkyl group; an optionally substituted $C_5$ to $C_{14}$, preferably $C_6$ to $C_{14}$, preferably $C_6$ to $C_{10}$, aryl group; an alkyl-aryl group of formula $-Q^{10}-Ar^{10}$ in which represents a $C_1$ to $C_9$, preferably $C_1$ to $C_5$, alkyl residue and $Ar^{10}$ represents a $C_6$ to $C_{14}$, preferably $C_6$, aryl group which is optionally substituted; a polyalkoxy group of formula $-(OCH_2CH_2)_n-OR^{15}$ in which n represents an integer between 2 and 5 and $R^{15}$ represents a $C_1$ to $C_{10}$, preferably $C_1$ to $C_5$, alkyl group; or a $C_1$ to $C_9$, preferably $C_1$ to $C_5$, alkoxy group;
- a heteroaryl group which preferably comprises from 5 to 10 members and which is optionally substituted, in particular by a $C_1$ to $C_9$, preferably $C_1$ to $C_5$, alkyl group; an optionally substituted $C_5$ to $C_{14}$, preferably $C_6$ to $C_{14}$, preferably $C_6$ to $C_{10}$, aryl group; an alkyl-aryl group of formula $-Q^{11}-Ar^{11}$ in which $Q^{11}$ represents a $C_1$ to $C_9$, preferably $C_1$ to $C_5$, alkyl residue and $Ar^{11}$ represents a $C_6$ to $C_{14}$, preferably $C_6$, aryl group which is optionally substituted; a polyalkoxy group of formula $-(OCH_2CH_2)_n-OR^{15}$ in which n represents an integer between 2 and 5 and $R^{15}$ represents a $C_1$ to $C_{10}$, preferably $C_1$ to $C_5$, alkyl group; or a $C_1$ to $C_9$, preferably $C_1$ to $C_5$, alkoxy group; or
- an alkyl-aryl group of formula $-Q^{12}-Ar^{12}$ in which $Q^{12}$ represents a $C_1$ to $C_9$, preferably $C_1$ to $C_5$, alkyl residue and $Ar^{12}$ represents a $C_6$ to $C_{14}$, preferably $C_6$, aryl group which is optionally substituted.

Preferably, in the process of the invention, $R^4$ and $R^5$, which are identical or different, represent:
- a linear or branched $C_1$ to $C_{10}$ alkyl group, for example methyl, ethyl, propyl or butyl;
- a $C_6$, $C_{10}$ or $C_{14}$ aryl group which is optionally substituted, in particular by a $C_1$ to $C_5$ alkyl group, for example methyl or ethyl; an optionally substituted phenyl group; an alkyl-aryl group of formula $-Q^9-Ar^9$ in which $Q^9$ represents a $C_1$ to $C_9$, preferably $C_1$ to $C_5$, alkyl residue and $Ar^9$ represents an optionally substituted phenyl group, preferably methylphenyl or ethylphenyl; a polyalkoxy group of formula $-(OCH_2CH_2)_n-OR^{15}$ in which n represents an integer between 2 and 5 and $R^{15}$ represents a $C_1$ to $C_{10}$, preferably $C_1$ to $C_5$, alkyl group; or a $C_1$ to $C_5$ alkoxy group, for example methoxy or ethoxy;
- a $C_5$ to $C_6$ cycloalkyl group which is optionally substituted, in particular by a $C_1$ to $C_5$ alkyl group, for example methyl or ethyl; an optionally substituted phenyl group; an alkyl-aryl group of formula $-Q^{10}-Ar^{10}$ in which $Q^{10}$ represents a $C_1$ to $C_9$, preferably $C_1$ to $C_5$, alkyl residue and $Ar^{10}$ represents an optionally substituted phenyl group, preferably methylphenyl or ethylphenyl; a polyalkoxy group of formula $-(OCH_2CH_2)_n-OR^{15}$ in which n represents an integer between 2 and 5 and $R^{15}$ represents a $C_1$ to $C_{10}$, preferably $C_1$ to $C_5$, alkyl group; or a $C_1$ to $C_5$ alkoxy group, for example methoxy or ethoxy;
- a heteroaryl group of aniline type which is optionally substituted, in particular by a $C_1$ to $C_5$ alkyl group, for example methyl or ethyl; an optionally substituted phenyl group; an alkyl-aryl group of formula $-Q^{11}-Ar^{11}$ in which $Q^{11}$ represents a $C_1$ to $C_9$, preferably $C_1$ to $C_5$, alkyl residue and $Ar^{11}$ represents an optionally substituted phenyl group, preferably methylphenyl or ethylphenyl; a polyalkoxy group of formula $-(OCH_2CH_2)_n-OR^{15}$ in which n represents an integer between 2 and 5 and $R^{15}$ represents a $C_1$ to $C_{10}$, preferably $C_1$ to $C_5$, alkyl group; or a $C_1$ to $C_5$ alkoxy group, for example methoxy or ethoxy; or
- an alkyl-aryl group of formula $-Q^{12}-Ar^{12}$ in which $Q^{12}$ represents a $C_1$ to $C_9$, preferably $C_1$ to $C_5$, alkyl residue and $Ar^{12}$ represents an optionally substituted phenyl group.

Advantageously, the alkyl carbonate is dimethyl carbonate or diethyl carbonate.

According to the invention, the term "alkylene carbonate" is understood to mean a compound of formula (IV)

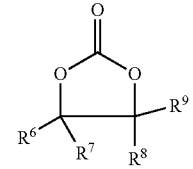

(IV)

in which:
$R^6$, $R^7$, $R^8$ and $R^9$, which are identical or different, are chosen from:
- a hydrogen;
- a linear, branched or cyclic $C_1$ to $C_g$, preferably $C_1$ to $C_5$, hydrocarbon group which can comprise one or more heteroatoms chosen in particular from oxygen, nitrogen or sulfur and which can comprise one or more OH substituents;
- a group of formula $-CH_2-R^{10}$, in which $R^{10}$ represents a linear, branched or cyclic $C_1$ to $C_9$, preferably $C_1$ to $C_5$, hydrocarbon group which can comprise one or more heteroatoms chosen in particular from oxygen, nitrogen or sulfur and which can comprise one or more OH substituents;
- a group of formula $C(O)OR^{11}$, in which $R^{11}$ represents a hydrogen atom or a $C_1$ to $C_9$, preferably $C_1$ to $C_5$, alkyl group, for example methyl or ethyl;
- a $C_5$ to $C_6$ cycloalkyl group which is optionally substituted, in particular by a $C_1$ to $C_9$, preferably $C_1$ to $C_5$, alkyl group; an optionally substituted $C_5$ to $C_{14}$, preferably $C_6$ to $C_{14}$, preferably $C_6$ to $C_{10}$, aryl group; an alkyl-aryl group of formula $-Q^{13}-Ar^{13}$ in which $Q^{13}$ represents a $C_1$ to $C_9$, preferably $C_1$ to $C_5$, alkyl residue and $Ar^{13}$ represents a $C_6$ to $C_{14}$, preferably $C_6$, aryl group which is optionally substituted; a polyalkoxy group of formula —$(OCH_2CH_2)_n$—$OR^{15}$ in which n represents an integer between 2 and 5 and $R^{15}$ represents a $C_1$ to $C_{10}$ preferably $C_1$ to $C_5$, alkyl group; or a $C_1$ to $C_9$, preferably $C_1$ to $C_5$, alkoxy group;

a heteroaryl group which is optionally substituted, in particular by a $C_1$ to $C_9$, preferably $C_1$ to $C_5$, alkyl group; an optionally substituted $C_5$ to $C_{14}$, preferably $C_6$ to $C_{14}$, preferably $C_6$ to $C_{10}$ aryl group; an alkyl-aryl group of formula -$Q^{14}$-$Ar^{14}$ in which $Q^{14}$ represents a $C_1$ to $C_9$, preferably $C_1$ to $C_5$, alkyl residue and $Ar^{14}$ represents a $C_6$ to $C_{14}$, preferably $C_6$, aryl group which is optionally substituted; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_9$, preferably $C_1$ to $C_5$, alkoxy group;

a $C_6$ to $C_{14}$ aryl group which is optionally substituted, in particular by a $C_1$ to $C_9$, preferably $C_1$ to $C_5$, alkyl group; an optionally substituted $C_5$ to $C_{14}$, preferably $C_6$ to $C_{14}$, preferably $C_6$ to $C_{10}$, aryl group; an alkyl-aryl group of formula $Q^{15}$-$Ar^{15}$ in which $Q^{15}$ represents a $C_1$ to $C_9$, preferably $C_1$ to $C_5$, alkyl residue and $Ar^{15}$ represents a $C_6$ to $C_{14}$, preferably $C_6$, aryl group which is optionally substituted; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_9$, preferably $C_1$ to $C_5$, alkoxy group;

an alkyl-aryl group of formula -$Q^{16}$-$Ar^{16}$ in which $Q^{16}$ represents a $C_1$ to $C_9$, preferably $C_1$ to $C_5$, alkyl residue and $Ar^{16}$ represents a $C_6$ to $C_{14}$, preferably $C_6$, aryl group which is optionally substituted;

or $R^6$ and $R^9$ form, together with the carbon atoms carrying them, a double bond;

or $R^6$ and $R^9$ form, together with the carbon atoms carrying them, a double bond which is included in an aryl group, in particular a phenyl group, formed by $R^7$ and $R^8$ with the two carbon atoms carrying them.

Preferably, in the process of the invention, $R^6$, $R^7$, $R^8$ and $R^9$, which are identical or different, are chosen from:

a hydrogen;

a linear or branched $C_1$ to $C_9$, preferably $C_1$ to $C_5$, alkyl group which can comprise one or more heteroatoms chosen in particular from oxygen, nitrogen or sulfur and which can comprise one or more OH substituents; for example methylene or ethylene;

a group of formula —$CH_2$—$R^{10}$ in which $R^{10}$ represents a linear or branched $C_1$ to $C_5$ hydrocarbon group which can comprise one or more heteroatoms chosen in particular from oxygen, nitrogen or sulfur and which can comprise one or more OH substituents, for example ethylene or methylene;

a group of formula $C(O)OR^{11}$ in which $R^{11}$ represents a hydrogen atom or a $C_1$ to $C_5$ alkyl group, for example methyl or ethyl;

a $C_5$ to $C_6$ cycloalkyl group which is optionally substituted, in particular by a $C_1$ to $C_5$ alkyl group, for example methyl or ethyl; an optionally substituted phenyl group; an alkyl-aryl group of formula -$Q^{13}$-$Ar^{13}$ in which $Q^{13}$ represents a $C_1$ to $C_9$, preferably $C_1$ to $C_5$, alkyl residue and $Ar^{13}$ represents an optionally substituted phenyl group, preferably methylphenyl or ethylphenyl; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_5$ alkoxy group, for example methoxy or ethoxy;

a heteroaryl group of aniline type which is optionally substituted, in particular by a $C_1$ to $C_5$ alkyl group, for example methyl or ethyl; an optionally substituted phenyl group; an alkyl-aryl group of formula -$Q^{14}$-$Ar^{14}$ in which $Q^{14}$ represents a $C_1$ to $C_9$, preferably $C_1$ to $C_5$, alkyl residue and $Ar^{14}$ represents an optionally substituted phenyl group, preferably methylphenyl or ethylphenyl; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_5$ alkoxy group, for example methoxy or ethoxy;

a $C_6$, $C_{10}$ or $C_{14}$ aryl group which is optionally substituted a $C_1$ to $C_5$ alkyl group, for example methyl or ethyl; an optionally substituted phenyl group; an alkyl-aryl group of formula -$Q^{15}$-$Ar^{15}$ in which $Q^{15}$ represents a $C_1$ to $C_9$, preferably $C_1$ to $C_5$, alkyl residue and $Ar^{15}$ represents an optionally substituted phenyl group, preferably methylphenyl or ethylphenyl; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_5$ alkoxy group, for example methoxy or ethoxy;

an alkyl-aryl group of formula -$Q^{16}$-$Ar^{16}$ in which $Q^{16}$ represents a $C_1$ to $C_9$, preferably $C_1$ to $C_5$, alkyl residue and $Ar^{16}$ represents an optionally substituted phenyl;

or $R^6$ and $R^9$ form, together with the carbon atoms carrying them, a double bond;

or $R^6$ and $R^9$ form, together with the carbon atoms carrying them, a double bond which is included in an aryl group, in particular a phenyl group, formed by $R^7$ and $R^8$ with the two carbon atoms carrying them.

Advantageously, the alkyl carbonate can be ethylene carbonate, propylene carbonate, dibutylene carbonate or dihexylene carbonate.

According to the invention, the catalytic entity of the catalytic system is a rare earth metal oxide or a mixture of rare earth metal oxides.

The term "rare earth metals" (Ln) is understood to mean the chemical elements chosen from the group formed by scandium, yttrium and the chemical elements having atomic numbers 57 to 71. Advantageously, the rare earth metals are chosen from cerium (Ce), lanthanum (La), praseodymium (Pr), neodymium (Nd), yttrium (Y), gadolinium (Gd), samarium (Sm) and holmium (Ho), alone or as mixtures, preferably cerium, lanthanum, praseodymium, samarium, yttrium and neodymium, or their mixtures.

According to the invention, the catalytic entity is chosen from $CeO_2$; $Pr_6O_{11}$; or rare earth metal oxides of formula $Ln_2O_3$ in which Ln represents lanthanum, neodymium, yttrium, gadolinium, samarium or holmium; or as a mixture.

Advantageously, the catalytic entity is chosen from $La_2O_3$, $CeO_2$, $Pr_6O_{11}$, $Nd_2C_3$, $Sm_2C_3$ or $Y_2C_3$, alone or as a mixture, preferably $La_2O_3$. Mention may in particular be made, as mixture, of the natural mixtures of rare earth metal oxides. Mention may be made, as specific mixture, for example, of $CeO_2/Pr_6O_{11}$.

In a preferred embodiment, the catalytic entity is $La_2O_3$.

In another preferred embodiment, the catalytic entity is $CeO_2$.

Generally, the catalytic system according to the invention is composed of a catalytic entity in the solid form, thus allowing it to be used in a continuous process. The catalyst can in particular be in the monolithic form (forming a single inert, rigid and porous block) or in the extruded form.

The catalytic system can also comprise an inert support on which the catalytic entity is deposited. The catalytic system comprising a support according to the invention can be in the extruded form, in the form of a coating having catalytic properties and based on rare earth metal oxide or mixture of rare earth metal oxides and optionally on a binder of known type on a substrate of metal or ceramic monolith type. Advantageously, it is in the extruded form. The extruded form advantageously makes it possible to carry out the process of the invention continuously, which is not possible with a powdered catalyst, which would obstruct the various elements of the reactor.

For the process according to the invention, the term "extruded catalytic system" is understood to mean any catalytic system obtained by ejection under pressure of a paste through the nozzles or dies having chosen shapes. The catalytic systems thus obtained can exhibit varied forms; they can, for example, exhibit cylindrical or semi-cylindrical, square or polygonal cross sections or also cross sections in the form of lobes, such as trilobes. The catalytic systems can be solid or hollow; they can have the monolith or honeycomb form. These extruded catalytic systems can be obtained in particular by the process as described on pages 4 to 10 of patent application WO98/24726.

The term "inert support" is understood to mean a support which does not participate, as catalyst or as reactant, in the transcarbonation reaction of the invention, this being the case whatever the pH. Typically, the support is neutral, that is to say that it does not substantially modify the catalytic activity of the catalytic entity. The support can also be described as inactive insofar as it does not exhibit a catalytic activity for the reaction and does not modify the catalytic activity of the catalytic entity. The supports are chosen from extrudable and nonhydrolyzable supports or monolithic and nonhydrolyzable supports.

Preferably, the support can be chosen from metal oxides which are extrudable and non hydrolyzable, clays, active charcoals (blacks) or ceramic or metal monoliths.

The support can, for example, be chosen from titanium oxides, zirconium oxides, iron oxides; aluminum oxides, such as alundum; silicas/aluminas, for example clays; active charcoals or kieselguhr.

It can also be corundum, silica carbide or pumice.

Mention may preferably be made, among extrudable and nonhydrolyzable metal oxides, of titanium oxides, zirconium oxides, iron oxides or aluminum oxides, preferably titanium oxides, zirconium oxides or neutral aluminas. More preferably, the support is chosen from titanium oxides, zirconium oxides, iron oxides, aluminum oxides, in particular neutral aluminas, or active charcoals, preferably titanium oxides, zirconium oxides, neutral aluminas or active charcoals.

The amount of catalytic entity on the support can be between 0.05% and 25% by weight, with respect to the total weight of the catalytic system, preferably from 1% to 10% by weight. It should be noted that this value depends in particular on the nature of the support, on its specific surface, on its porosity and on the catalytic properties desired.

According to the invention, the catalytic system can in particular exhibit a specific surface of at least 1 m²/g; preferably, the specific surface is between 1 and 150 m²/g, more preferably between 3 and 100 m²/g. A person skilled in the art is able to adjust this specific surface, for example by calcination of the catalytic system.

According to the invention, the catalytic system can be doped with metals of the Lewis acid type, for example transition metals, alkaline earth metals and semi-metals. Advantageously, these catalytic entities form, with the dopants, solid solutions forming a unit entity.

These metals can be chosen from iron (Fe(II) and Fe(III)), copper (Cu(I) and Cu(II)), aluminum (Al(III)), titanium (Ti(IV)), boron (B(III)), zinc (Zn(II)) and magnesium (Mg(II)). Preferably, these metals are chosen from the group consisting of iron (Fe(II) and Fe(III)), copper (Cu(I) and Cu(II)), titanium (Ti(IV)) and zinc (Zn(II)).

In the process of the invention, the relative percentage of metal, with respect to the catalyst, can be between 0.01% and 10% by weight, preferably between 1% and 10% by weight, for example between 1% and 5% by weight.

Advantageously, the catalytic systems of the invention are stable toward water. For example, the catalysts of the invention can comprise less than 5% of water. This advantageously makes it possible to carry out the transcarbonation reaction in a medium comprising water, for example in a medium comprising less than 15% of water, for example less than 5% of water. Thus, and contrary to the process of the state of the art, it is not necessary to have close control of the amount of water in the reaction medium and it is not necessary to employ reactants devoid of water. This exhibits in particular advantages in terms of costs.

The catalyst according to the invention can advantageously be easily recovered after reaction by any method known to a person skilled in the art, in particular by settling or filtration.

The process according to the invention is carried out at atmospheric pressure or autogenous pressure.

The term "autogenous pressure" is understood to mean the pressure inside the reactor which is due to the reactants used. In the case of the present invention, the term "autogenous pressure" is understood to mean a pressure of less than 1 MPa, preferably of less than 0.5 MPa, preferably of less than 0.3 MPa, for example of less than 0.2 MPa.

According to the invention, the process according to the invention is carried out at a temperature of between 25 and 250° C., preferably between 25 and 200° C., for example between 50 and 125° C.

Advantageously, the polyol/alkyl carbonate or polyol/alkylene carbonate molar ratio is between 1/6 and 1/1, preferably between 1/4 and 1/1, for example between 1/3 and 1/1.

Advantageously, the amount of catalyst is between 0.01% and 50% by weight, with respect to the weight of polyol, preferably between 1% and 25% by weight, preferably between 3% and 15% by weight.

The process according to the invention makes it possible to obtain the compound of formula (I) with good yields and a selectivity of greater than 90%, ranging even up to 99%.

Advantageously, the process according to the invention is carried out in the absence of solvent. The polyol can act as solvent in the reaction according to the invention.

The process according to the invention can be carried out continuously or batchwise.

Advantageously, the process according to the invention is carried out continuously.

According to the invention, the process can comprise a preliminary stage of preparation of the alkyl carbonate or alkylene carbonate. This preliminary stage is carried out by reaction between an alcohol or mixture of alcohols or a diol and $CO_2$ in the presence of a catalytic system composed of a catalytic entity chosen from rare earth metal oxides and mixtures of rare earth metal oxides and optionally of a support.

The catalytic entity and the support are as defined for the transcarbonation process according to the invention.

Advantageously, the molar ratio of alcohol or diol to $CO_2$ is between 1 and 150 molar equivalents, preferably between 1 and 100 equivalents.

According to the invention, the preliminary stage of preparation of the alkyl carbonate or alkylene carbonate is carried out at autogenous pressure or at atmospheric pressure.

According to the invention, the preliminary stage of preparation of the alkyl carbonate or alkylene carbonate is carried out at a temperature of between 25 and 250° C., preferably between 25 and 200° C., for example between 50 and 150° C.

Advantageously, the amount of catalytic system is between 0.01% and 50% by weight, with respect to the weight of alcohol, of mixture of alcohols or of diol, preferably between 1% and 25% by weight, preferably between 3% and 15% by weight.

According to the invention, the alcohol corresponds to the formula $R^{12}OH$ in which $R^{12}$ represents:
- a linear or branched $C_1$ to $C_{20}$ alkyl group;
- a $C_5$ to $C_{14}$ aryl group which is optionally substituted, in particular by a $C_1$ to $C_9$, preferably $C_1$ to $C_5$, alkyl group; an optionally substituted $C_5$ to $C_{14}$, preferably $C_6$ to $C_{14}$, preferably $C_6$ to $C_{10}$, aryl group; an alkyl-aryl group of formula -$Q^9$-$Ar^9$ in which $Q^9$ represents a $C_1$ to $C_9$, preferably $C_1$ to $C_5$, alkyl residue and $Ar^9$ represents a $C_6$ to $C_{14}$, preferably $C_6$, aryl group which is optionally substituted; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_9$, preferably $C_1$ to $C_5$, alkoxy group;
- a $C_5$ to $C_6$ cycloalkyl group which is optionally substituted, in particular by a $C_1$ to $C_9$, preferably $C_1$ to $C_5$, alkyl group; an optionally substituted $C_5$ to $C_{14}$, preferably $C_6$ to $C_{14}$, preferably $C_6$ to $C_{10}$, aryl group; an alkyl-aryl group of formula -$Q^{10}$-$Ar^{10}$ in which $Q^{10}$ represents a $C_1$ to $C_9$, preferably $C_1$ to $C_5$, alkyl residue and $Ar^{10}$ represents a $C_6$ to $C_{14}$, preferably $C_6$, aryl group which is optionally substituted; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_9$, preferably $C_1$ to $C_5$, alkoxy group;
- a heteroaryl group which preferably comprises from 5 to 10 members and which is optionally substituted, in particular by a $C_1$ to $C_9$, preferably $C_1$ to $C_5$, alkyl group; an optionally substituted $C_5$ to $C_{14}$, preferably $C_6$ to $C_{14}$, preferably $C_6$ to $C_{10}$, aryl group; an alkyl-aryl group of formula -$Q^{11}$-$Ar^{11}$ in which $Q^{11}$ represents a $C_1$ to $C_9$, preferably $C_1$ to $C_5$, alkyl residue and $Ar^{11}$ represents a $C_6$ to $C_{14}$, preferably $C_6$, aryl group which is optionally substituted; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_9$, preferably $C_1$ to $C_5$, alkoxy group; or
- an alkyl-aryl group of formula -$Q^{12}$-$Ar^{12}$ in which $Q^{12}$ represents a $C_1$ to $C_9$, preferably $C_1$ to $C_5$, alkyl residue and $Ar^{12}$ represents a $C_6$ to $C_{14}$, preferably $C_6$, aryl group which is optionally substituted.

Preferably, in the process of the invention, $R^{12}$ represents:
- a linear or branched $C_1$ to $C_{10}$ alkyl group, for example methyl, ethyl, propyl or butyl;
- a $C_6$, $C_{10}$ or $C_{14}$ aryl group which is optionally substituted, in particular by a $C_1$ to $C_5$ alkyl group, for example methyl or ethyl; an optionally substituted phenyl group; an alkyl-aryl group of formula -$Q^9$-$Ar^9$ in which $Q^9$ represents a $C_1$ to $C_9$, preferably $C_1$ to $C_5$, alkyl residue and $Ar^9$ represents an optionally substituted phenyl group, preferably methylphenyl or ethylphenyl; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_5$ alkoxy group, for example methoxy or ethoxy;
- a $C_5$ to $C_6$ cycloalkyl group which is optionally substituted, in particular by a $C_1$ to $C_5$ alkyl group, for example methyl or ethyl; an optionally substituted phenyl group; an alkyl-aryl group of formula -$Q^{10}$-$Ar^{10}$ in which $Q^{10}$ represents a $C_1$ to $C_9$, preferably $C_1$ to $C_5$, alkyl residue and $Ar^{10}$ represents an optionally substituted phenyl group, preferably methylphenyl or ethylphenyl; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_5$ alkoxy group, for example methoxy or ethoxy;
- a heteroaryl group of aniline type which is optionally substituted, in particular by a $C_1$ to $C_5$ alkyl group, for example methyl or ethyl; an optionally substituted phenyl group; an alkyl-aryl group of formula -$Q^{11}$-$Ar^{11}$ in which $Q^{11}$ represents a $C_1$ to $C_9$, preferably $C_1$ to $C_5$, alkyl residue and $Ar^{11}$ represents an optionally substituted phenyl group, preferably methylphenyl or ethylphenyl; a polyalkoxy group of formula —$(OCH_2CH_2)_n$—$OR^{15}$ in which n represents an integer between 2 and 5 and $R^{15}$ represents a $C_1$ to $C_{10}$, preferably $C_1$ to $C_5$, alkyl group; or a $C_1$ to $C_5$ alkoxy group, for example methoxy or ethoxy; or
- an alkyl-aryl group of formula -$Q^{12}$-$Ar^{12}$ in which $Q^{12}$ represents a $C_1$ to $C_9$, preferably $C_1$ to $C_5$, alkyl residue and $Ar^{12}$ represents an optionally substituted phenyl group.

According to the invention, the diol corresponds to the formula (V)

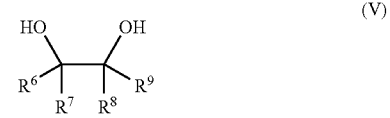

in which:
$R^6$, $R^7$, $R^8$ and $R^9$, which are identical or different, are as defined above.

In the process of the invention, when several polyalkoxy groups are present, the n and $R^{15}$ values are chosen independently of one another and can be identical or different.

In the process of the invention, the preferences for the compounds of formulae (II) and (III) or (II) and (IV), taken in any combination, make it possible to define a subgroup of compound of formula (I).

In the process of the invention, the preferences for the compound of formula (V) make it possible to define a subgroup of compound of formula (IV).

In the process of the invention, the preferences for the alcohol make it possible to define a subgroup of compound of formula (III).

The catalytic system can be identical or different in the preliminary stage and in the transcarbonation stage.

Advantageously, the catalytic system is the same in the preliminary stage and in the transcarbonation stage.

Advantageously, the preliminary stage and the transcarbonation stage of the process according to the invention are carried out in just one sequence, continuously. The catalytic system can be identical or different in the preliminary stage and in the transcarbonation stage; advantageously, the catalytic system is identical for the two reactions.

Advantageously, the process according to the invention is carried out in the absence of solvent.

The term "continuous process" is understood to mean a process in which the reactants are fed continuously into the reactor and the products are withdrawn continuously from the reaction medium and are then separated. The unreacted reactants can be reintroduced into the reaction medium or else discarded.

According to the invention, the continuous process is carried out with short residence times of the reactants in the reactor. The term "short residence times" is understood to mean times of between 1 and 24 hours, preferably between 1 and 5 hours.

The invention will now be described with the help of examples, the latter being given by way of illustration without, however, being limiting.

EXAMPLES

The yields are molar yields of glycerol carbonate, with respect to the molar amount of starting glycerol. The yields are determined by gas chromatography using a Stabilwax® capillary column (polar phase; crossbond carbowax polyethylene glycol). Tetraethylene glycol (99%, Alfa) is used as internal standard. The glycerol (>99%, Sigma-Aldrich), the ethylene carbonate (>99%, Acros) and the dimethyl carbonate (99%, Alfa) are commercial products.

Example 1

Preparation of Glycerol Carbonate by Reaction of Glycerol with Ethylene Carbonate (Catalyst $La_2O_2$)

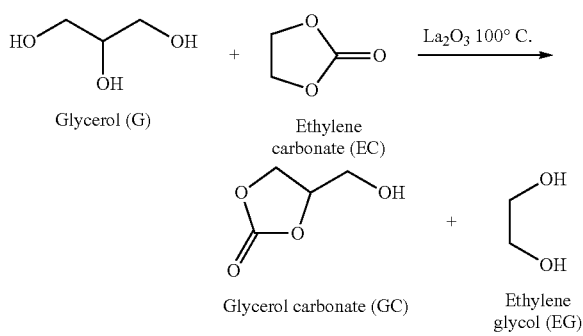

250 mg of glycerol (2.7 mmol), 240 mg of ethylene carbonate (2.7 mmol) and 88.5 mg of $La_2O_3$ (10 mol %), calcined at 500° C., are mixed (EC/G molar ratio=1). The reaction mixture is brought to 100° C. with magnetic stirring for 24 hours. After cooling to ambient temperature, the crude reaction mixture is analyzed directly by gas chromatography. Glycerol carbonate is obtained with a molar yield of 60% (192 mg), with respect to the glycerol, with a selectivity of greater than 99%.

The process according to the invention, carried out with an ethylene carbonate/glycerol ratio of 1/1, makes it possible to prepare glycerol carbonate with a good yield and a good selectivity.

Example 2

Preparation of Glycerol Carbonate by Reaction of Glycerol with Ethylene Carbonate (Catalyst $La_2O_3$—Molar Ratio of 1 to 3)

A series of tests on the synthesis of glycerol carbonate is carried out as described in example 1, in which the glycerol and the ethylene carbonate are mixed according to the molar ratios shown in table 1.

TABLE 1

| Example | EC/G Ratio[a] | Amount of EC (mg) | Amount cat[b] (mol %) | Temp. (° C.) | GC Yield (%)[c] |
|---|---|---|---|---|---|
| 1 | 1 | 239 | 10 | 100 | 60 |
| 2 | 1.2 | 287 | 10 | 100 | 64 |
| 3 | 1.5 | 359 | 10 | 100 | 78 |
| 4 | 2 | 478 | 10 | 100 | 91 |
| 5 | 3 | 717 | 10 | 100 | 95 |

[a]molar ratio,
[b]mol of catalyst, with respect to the number of moles of glycerol;
[c]molar yield obtained, with respect to the number of moles of glycerol The process according to the invention, carried out with an ethylene carbonate/glycerol ratio of between 1/1 and 3/1, makes it possible to prepare glycerol carbonate with a good yield and a good selectivity.

Example 3

Variation in the Amount of Catalyst

A series of tests on the synthesis of glycerol carbonate is carried out as described in example 1, the amount of catalyst used being varied. The results are shown in table 2.

TABLE 2

| Example | EC/G Ratio[a] | Cat./G Ratio by weight[b] | Amount cat[c] (mol %) | Temp. (° C.) | GC Yield (%)[d] |
|---|---|---|---|---|---|
| 6 | 1 | 35.4 | 10 | 100 | 60 |
| 7 | 1 | 17.7 | 5 | 100 | 60 |
| 8 | 1 | 3.54 | 1 | 100 | 24 |

[a]molar ratio;
[b]catalyst/glycerol ratio by weight;
[c]mol of catalyst, with respect to the number of moles of glycerol;
[d]molar yield obtained, with respect to the number of moles of glycerol The process according to the invention makes it possible to prepare glycerol carbonate with a good yield and in particular a good selectivity. The reduction in the amount of catalyst makes it possible to retain a good yield and a good selectivity.

Example 4

Glycerol Carbonate Yield as a Function of the Reaction Time

A series of tests on the synthesis of glycerol carbonate is carried out as described in example 1, the reaction time being varied. The results are shown in table 3.

TABLE 3

| Example | EC/G Ratio[a] | Amount of EC (mg) | Amount cat[b] (mol %) | Time (h) | Temp. (° C.) | GC Yield (%)[c] |
|---|---|---|---|---|---|---|
| 9 | 1 | 239 | 10 | 24 | 100 | 60 |
| 10 | 1 | 239 | 10 | 5 | 100 | 57 |
| 11 | 3 | 717 | 10 | 24 | 100 | 95 |
| 12 | 3 | 717 | 10 | 5 | 100 | 96 |

[a] molar ratio;
[b] mol of catalyst, with respect to the number of moles of glycerol;
[c] molar yield obtained, with respect to the number of moles of glycerol The process according to the invention makes it possible to prepare glycerol carbonate with a good yield and in particular a good selectivity, this being the case even with greatly reduced reaction times.

Example 5

Preparation of Glycerol Carbonate from Ethylene Carbonate and Glycerol with Different Catalysts A series of tests on the synthesis of glycerol carbonate is carried out as described in example 1 but using different catalysts. The results are shown in tables 4 and 5.

TABLE 4

| Example | Catalyst | EC/G Ratio[a] | Amount cat[b] (mol %) | Temp. (° C.) | GC Yield (%)[c] |
|---|---|---|---|---|---|
| 13 | $La_2O_3$ | 1 | 10 | 100 | 60 |
| 14 (comparative example) | CaO | 1 | 10 | 100 | 55 |
| 15 | $Pr_6O_{11}$ | 1 | 10 | 100 | 63 |
| 16 | $CeO_2$ | 1 | 10 | 100 | 49 |
| 17 | $CeO_2/ZrO_2$ | 1 | 10 | 100 | 51 |
| 18 | $CeO_2$ 90.6% | 1 | 10 | 100 | 51 |
| 19 | $CeO_2/Pr_6O_{11}$ | 1 | 10 | 100 | 45 |

[a] molar ratio;
[b] mol of catalyst, with respect to the number of moles of glycerol;
[c] molar yield obtained, with respect to the number of moles of glycerol

TABLE 5

| Example | Catalyst | EC/G Ratio[a] | Amount cat[b] (mol %) | Temp. (° C.) | GC Yield (%)[c] |
|---|---|---|---|---|---|
| 20 | $La_2O_3$ | 4 | 10 | 100 | 92 |
| 21 (comparative example) | CaO | 4 | 10 | 100 | 90 |
| 22 | $Pr_6O_{11}$ | 4 | 10 | 100 | 91 |
| 23 (comparative example) | $Al_2O_3$ | 4 | 10 | 100 | 78 |
| 24 | $CeO_2$ | 4 | 10 | 100 | 89 |
| 25 | $CeO_2/ZrO_2$ | 4 | 10 | 100 | 99 |
| 26 | $CeO_2$ 90.6% (percentage of purity) | 4 | 10 | 100 | 80 |
| 27 | $CeO_2/Pr_6O_{11}$ | 4 | 10 | 100 | 85 |

[a] molar ratio;
[b] mol of catalyst, with respect to the number of moles of glycerol;
[c] molar yield obtained, with respect to the number of moles of glycerol The process according to the invention makes it possible to prepare glycerol carbonate with a good yield and a good selectivity.

Example 6

Preparation of Glycerol Carbonate by Reaction of Glycerol with Dimethyl Carbonate Catalyzed by $La_2O_3$ $$\text{Glycerol (G)} + \text{Dimethyl carbonate (DMC)} \xrightarrow{La_2O_3} \text{Glycerol carbonate (GC)} + 2 \times \text{MeOH}$$

250 mg of glycerol (2.7 mmol), 244 mg of dimethyl carbonate (2.7 mmol) and 88.5 mg of $La_2O_3$ (10 mol %), calcined at 500° C., are mixed (dimethyl carbonate/glycerol molar ratio=1). The reaction mixture is brought to 100° C. with magnetic stirring for 24 hours. After cooling to ambient temperature, the crude reaction mixture is analyzed directly by gas chromatography. Glycerol carbonate is obtained with a molar yield of 35% (85 mg), with respect to the glycerol, with a selectivity of greater than 99%. The results were determined by proton NMR.

The process according to the invention makes it possible to prepare glycerol carbonate with a good selectivity.

Example 7

Variation in the DMC/G ratio

A series of tests on the synthesis of glycerol carbonate is carried out under the same conditions as example 6, in which the glycerol and the dimethyl carbonate are mixed according to the molar ratios shown in table 6.

TABLE 6

| Example | DMC/G Ratio[a] | Amount of DMC (mg) | Amount cat[b] (mol %) | Temp. (° C.) | GC Yield (%)[c] |
|---|---|---|---|---|---|
| 28 | 1 | 244 | 10 | 100 | 35 |
| 29 | 1.5 | 366 | 10 | 100 | 45 |
| 30 | 2 | 489 | 10 | 100 | 56 |
| 31 | 3 | 733 | 10 | 100 | 80 |
| 32 | 4 | 978 | 10 | 100 | 90 |

[a] molar ratio;
[b] mol of catalyst, with respect to the number of moles of glycerol;
[c] molar yield obtained, with respect to the number of moles of glycerol The process according to the invention makes it possible to prepare glycerol carbonate with a good yield and in particular a good selectivity.

Example 8

Variation in the Catalyst

A series of tests on the synthesis of glycerol carbonate is carried out as described in example 6 but using other catalysts. The results are listed in table 7.

TABLE 7

| Example | Catalyst | DMC/G Ratio[a] | Amount cat[b] (mol %) | Temp. (° C.) | GC Yield (%)[c] |
|---|---|---|---|---|---|
| 33 | La$_2$O$_3$ | 4 | 10 | 100 | 96 |
| 34 (comparative example) | CaO | 4 | 10 | 100 | 95 |
| 35 | Pr$_6$O$_{11}$ | 4 | 10 | 100 | 50 |
| 36 (comparative example) | Al$_2$O$_3$ | 4 | 10 | 100 | 35 |

[a] molar ratio;
[b] mol of catalyst, with respect to the number of moles of glycerol;
[c] molar yield obtained, with respect to the number of moles of glycerol The process according to the invention makes it possible to prepare glycerol carbonate with a good yield and a good selectivity for different catalysts.

Example 9

Comparative Examples of Transcarbonation Using a Rare Earth Metal Catalyst of Formula La$_2$CO$_3$ and a Catalyst which is a Mixture of Lanthanum Phosphate and Cerium Phosphate

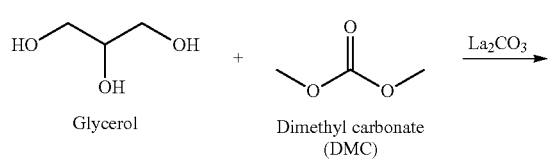

Glycerol + Dimethyl carbonate (DMC) →(La$_2$CO$_3$)

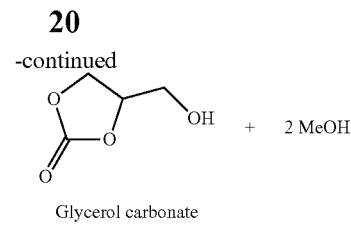

Glycerol carbonate + 2 MeOH

Preparation of Glycerol Carbonate by Reaction of Glycerol with Dimethyl Carbonate Catalyzed by La$_2$CO$_3$ 1.26 g of glycerol (13.7 mmol), 4.94 g of dimethyl carbonate (54.8 mmol) and 0.628 mg of La$_2$CO$_3$ (10 mol %) are mixed. The reaction mixture is brought to 100° C. with magnetic stirring for 24 hours. After cooling to ambient temperature, the crude reaction mixture is analyzed directly by gas chromatography. Glycerol carbonate is obtained with a molar yield of 3%, with respect to the glycerol, with a selectivity of greater than 99%. The results were determined by proton NMR.

The yield is very low in comparison with the yield obtained with the process according to the invention.

Preparation of Glycerol Carbonate by Reaction of Glycerol with Dimethyl Carbonate Catalyzed by a La/Ce Phosphate (LaPO$_4$/CePO$_4$) Mixture 1.26 g of glycerol (13.7 mmol), 4.94 g of dimethyl carbonate (54.8 mmol) and 0.771 mg of LaPO$_4$/CePO$_4$ (10 mol %) are mixed. The reaction mixture is brought to 100° C. with magnetic stirring for 24 hours. After cooling to ambient temperature, the crude reaction mixture is analyzed directly by gas chromatography.

No conversion of the glycerol to glycerol carbonate was observed (Yield 0%).

The invention claimed is:

1. A process for the preparation by transcarbonation of a compound of formula (I),

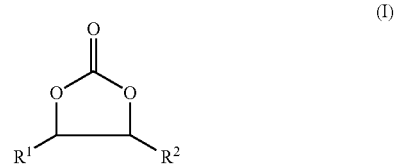

(I)

in which:
R$^1$ represents:
  a hydrogen atom;
  a linear, branched or cyclic C$_1$ to C$_9$ hydrocarbon group optionally comprising one or more heteroatoms and/or one or more OH substituents;
  a group of formula —CH$_2$—R$^3$ in which R$^3$ represents a linear or branched C$_1$ to C$_9$ hydrocarbon group optionally comprising one or more heteroatoms and/or one or more OH substituents;
  an alkyl-aryl group of formula -Q$^1$-Ar$^1$ in which Q$^1$ represents a C$_1$ to C$_9$ alkyl group and Ar$^1$ represents a C$_6$ to C$_{14}$ aryl group which is optionally substituted;
  a C$_6$ to C$_{14}$ aryl group which is unsubstituted or is substituted by a C$_1$ to C$_9$ alkyl group, an optionally substituted C$_6$ to C$_{14}$ aryl group, an alkyl-aryl group of formula -Q$^2$-Ar$^2$ in which Q$^2$ represents a C$_1$ to C$_9$ alkyl residue and Ar$^2$ represents a C$_6$ to C$_{14}$ aryl group which is optionally substituted, a polyalkoxy group of formula —(OCH$_2$CH$_2$)$_n$—OR$^{15}$ in which n represents an integer between 2 and 5 and R$^{15}$ represents a C$_1$ to C$_{10}$ alkyl group, or a C$_1$ to C$_9$ alkoxy group;

a heteroaryl group which is unsubstituted, or is substituted by a C$_1$ to C$_9$ alkyl group, a C$_5$ to C$_{14}$ aryl group, an alkyl-aryl group of formula -Q$^3$-Ar$^3$ in which Q$^3$ represents a C$_1$ to C$_9$ alkyl residue and Ar$^3$ represents a C$_6$ to C$_{14}$ aryl group which is optionally substituted, a polyalkoxy group of formula —(OCH$_2$CH$_2$)$_n$—OR$^{15}$ in which n represents an integer between 2 and 5 and R$^{15}$ represents a C$_1$ to C$_{10}$ alkyl group, or a C$_1$ to C$_9$ alkoxy group; and R$^2$ represents:

a hydrogen atom;

a linear or branched C$_1$ to C$_{10}$ alkyl group;

a group of formula -L$^1$OH in which L$^1$ represents:

a linear, branched or cyclic C$_1$ to C$_9$ hydrocarbon optionally comprising one or more heteroatoms and/or one or more OH substituents;

an alkyl-aryl group of formula -Q$^4$-Ar$^4$ in which Q$^4$ represents a C$_1$ to C$_9$ alkyl residue and Ar$^4$ represents a C$_6$ to C$_{14}$ aryl group which is optionally substituted;

a group of formula -L$^2$-CH$_2$ in which L$^2$ represents:

a linear, branched or cyclic C$_1$ to C$_9$ hydrocarbon group optionally comprising one or more heteroatoms and/or one or more pendant OH groups;

a C$_5$ to C$_{14}$ aryl group which is unsubstituted, or is substituted by a C$_1$ to C$_9$ alkyl group, an optionally substituted C$_5$ to C$_{14}$ aryl group, an alkyl-aryl group of formula -Q$^5$-Ar$^5$ in which Q$^5$ represents a C$_1$ to C$_9$ alkyl residue and Ar$^5$ represents a C$_6$ to C$_{14}$ aryl group which is optionally substituted, a polyalkoxy group of formula —(OCH$_2$CH$_2$)$_n$—OR$^{15}$ in which n represents an integer between 2 and 5 and R$^{15}$ represents a C$_1$ to C$_{10}$ alkyl group, or a C$_1$ to C$_9$ alkoxy group;

a heteroaryl group which is unsubstituted, or is substituted by a C$_1$ to C$_9$ alkyl group, an optionally substituted C$_6$ to C$_{14}$ aryl group, an alkyl-aryl group of formula -Q$^6$-Ar$^6$ in which Q$^6$ represents a C$_1$ to C$_9$ alkyl residue and Ar$^6$ represents a C$_6$ to C$_{14}$ aryl group which is optionally substituted, a polyalkoxy group of formula —(OCH$_2$CH$_2$)$_n$—OR$^{15}$ in which n represents an integer between 2 and 5 and R$^{15}$ represents a C$_1$ to C$_{10}$ alkyl group, or a C$_1$ to C$_9$ alkoxy group;

a C$_6$ to C$_{14}$ aryl group which is unsubstituted, or is substituted by a C$_1$ to C$_9$ alkyl group, an optionally substituted C$_6$ to C$_{14}$ aryl group, an alkyl-aryl group of formula -Q$^5$-Ar$^5$ in which Q$^5$ represents a C$_1$ to C$_9$ alkyl residue and Ar$^5$ represents a C$_6$ to C$_{14}$ aryl group which is optionally substituted, a polyalkoxy group of formula —(OCH$_2$CH$_2$)$_n$—OR$^{15}$ in which n represents an integer between 2 and 5 and R$^{15}$ represents a C$_1$ to C$_{10}$ alkyl group, or a C$_1$ to C$_9$ alkoxy group; or a heteroaryl group which is unsubstituted, or is substituted by a C$_1$ to C$_9$ alkyl group, an optionally substituted C$_6$ to C$_{14}$ aryl group, an alkyl-aryl group of formula -Q$^6$-Ar$^6$ in which Q$^6$ represents a C$_1$ to C$_9$ alkyl residue and Ar$^6$ represents a C$_6$ to C$_{14}$ aryl group which is optionally substituted, a polyalkoxy group of formula —(OCH$_2$CH$_2$)$_n$—OR$^{15}$ in which n represents an integer between 2 and 5 and R$^{15}$ represents a C$_1$ to C$_{10}$ alkyl group, or a C$_1$ to C$_9$ alkoxy group;

the process comprising the reaction, in the presence of a catalytic system that is extruded, between a polyol of formula (II)

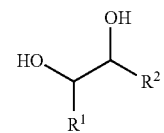

and an alkyl carbonate or an alkylene carbonate, the catalytic system consisting of a rare earth metal oxide of formula CeO$_2$, Pr$_6$O$_{11}$, Ln$_2$O$_3$, or mixtures of said rare earth metal oxides thereof, Ln representing lanthanum, neodymium, yttrium, gadolinium, samarium or holmium, wherein the process is carried out in the presence of water, wherein the amount of water in the reaction medium is less than 15%.

2. The process as claimed in claim 1, wherein alkyl carbonate is a compound of formula (III)

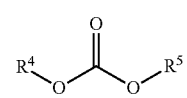

in which R$^4$ and R$^5$, which are identical or different, represent:

a linear or branched C$_1$ to C$_{20}$ alkyl group;

a C$_5$ to C$_6$ cycloalkyl group which is unsubstituted or is substituted by a C$_1$ to C$_9$ alkyl group, an optionally substituted C$_6$ to C$_{14}$ aryl group, an alkyl-aryl group of formula -Q$^{10}$-Ar$^{10}$ in which Q$^{10}$ represents a C$_1$ to C$_9$ alkyl residue and Ar$^{10}$ represents a C$_6$ to C$_{14}$ aryl group which is optionally substituted, a polyalkoxy group of formula —(OCH$_2$CH$_2$)$_n$—OR$^{15}$ in which n represents an integer between 2 and 5 and R$^{15}$ represents a C$_1$ to C$_{10}$ alkyl group, or a C$_1$ to C$_9$ alkoxy group; or an alkyl-aryl group of formula -Q$^{12}$-Ar$^{12}$ in which Q$^{12}$ represents a C$^1$ to C$_9$ alkyl residue and Ar$^{12}$ represents a C$_6$ to C$_{14}$ aryl group which is optionally substituted.

3. The process as claimed in claim 1, wherein the alkylene carbonate is a compound of formula (IV)

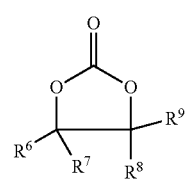

in which R$^6$, R$^7$, R$^8$ and R$^9$, which are identical or different, represent:

a hydrogen;

a linear, branched or cyclic C$_1$ to C$_9$ hydrocarbon group which can comprise one or more heteroatoms and which can comprise one or more OH substituents;

a group of formula —CH$_2$—R$^{10}$ in which R$^{10}$ represents a linear, branched or cyclic C$_1$ to C$_9$ hydrocarbon group which can comprise one or more heteroatoms and which can comprise one or more OH substituents;

a group of formula C(O)OR$^{11}$ in which R$^{11}$ represents a hydrogen atom or a C$_1$ to C$_9$ alkyl group;

a $C_5$ to $C_6$ cycloalkyl group which is unsubstituted, or substituted by a $C_1$ to $C_9$ alkyl group, an optionally substituted $C_6$ to $C_{14}$ aryl group, an alkyl-aryl group of formula -$Q^{13}$-$Ar^{13}$ in which $Q^{13}$ represents a $C_1$ to $C_9$ alkyl residue and $Ar^{13}$ represents a $C_6$ to $C_{14}$ aryl group which is optionally substituted, a polyalkoxy group of formula —$(OCH_2CH_2)_n$—$OR^{15}$ in which n represents an integer between 2 and 5 and $R^{15}$ represents a $C_1$ to $C_{10}$ alkyl group, or a $C_1$ to $C_9$ alkoxy group;

a heteroaryl group which is unsubstituted, or is substituted by a $C_1$ to $C_9$ alkyl group, an optionally substituted $C_6$ to $C_{14}$ aryl group, an alkyl-aryl group of formula -$Q^{14}$-$Ar^{14}$ in which $Q^{14}$ represents a $C_1$ to $C_9$ alkyl residue and $Ar^{14}$ represents a $C_6$ to $C_{14}$ aryl group which is optionally substituted, a polyalkoxy group of formula —$(OCH_2CH_2)_n$—$OR^{15}$ in which n represents an integer between 2 and 5 and $R^{15}$ represents a $C_1$ to $C_{10}$ alkyl group, or a $C_1$ to $C_9$ alkoxy group;

a $C_6$ to $C_{14}$ aryl group which is unsubstituted, or is substituted by a $C_1$ to $C_9$ alkyl group, an optionally substituted $C_6$ to $C_{14}$ aryl group, an alkyl-aryl group of formula -$Q^{15}$-$Ar^{15}$ in which $Q^{15}$ represents a $C_1$ to $C_9$ alkyl residue and $Ar^{15}$ represents a $C_6$ to $C_{14}$ aryl group which is optionally substituted, a polyalkoxy group of formula —$(OCH_2CH_2)_n$—$OR^{15}$ in which n represents an integer between 2 and 5 and $R^{15}$ represents a $C_1$ to $C_{10}$ alkyl group, or a $C_1$ to $C_9$ alkoxy radical;

an alkyl-aryl group of formula -$Q^{16}$-$Ar^{16}$ in which $Q^{16}$ represents a $C_1$ to $C_9$ alkyl residue and $Ar^{16}$ represents a $C_6$ to $C_{14}$ aryl group which is optionally substituted;

or $R^6$ and $R^9$ form, together with the carbon atoms carrying them, a double bond;

or $R^6$ and $R^9$ form, together with the carbon atoms carrying them, a double bond which is included in an aryl group, in particular a phenyl group, formed by $R^7$ and $R^8$ with the two carbon atoms carrying them.

4. The process as claimed in claim 1, wherein the compound of formula (I) is a compound of formula (Ia)

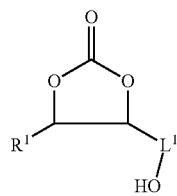

(Ia)

and the polyol of formula (II) is a polyol of formula (IIa)

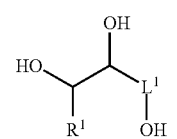

(IIa)

in which $R^1$ and $L^1$ are as defined in claim 1.

5. The process as claimed in claim 1, additionally comprising a preliminary stage of preparation of the alkyl carbonate or alkylene carbonate by reaction between an alcohol or mixture of alcohols or a diol and $CO_2$ in the presence of a catalytic system comprising a catalytic entity chosen from rare earth metal oxides or mixtures of rare earth metal oxides and optionally of an inert support.

6. The process as claimed in claim 5, wherein the alcohol is of formula $R^{12}OH$ in which $R^{12}$ represents:

a linear or branched $C_1$ to $C_{20}$ alkyl group;

a $C_6$ to $C_{14}$ aryl group which is unsubstituted, or is substituted by a $C_1$ to $C_9$ alkyl group, an optionally substituted $C_6$ to $C_{14}$ aryl group, an alkyl-aryl group of formula -$Q^9$-$Ar^9$ in which $Q^9$ represents a $C_1$ to $C_9$ alkyl residue and $Ar^9$ represents a $C_6$ to $C_{14}$ aryl group which is optionally substituted, a polyalkoxy group of formula —$(OCH_2CH_2)_n$—$OR^{15}$ in which n represents an integer between 2 and 5 and $R^{15}$ represents a $C_1$ to $C_{10}$ alkyl group, or a $C_1$ to $C_9$ alkoxy group;

a $C_5$ to $C_6$ cycloalkyl group which is unsubstituted, or is substituted by a $C_1$ to $C_9$ alkyl group, an optionally substituted $C_6$ to $C_{14}$ aryl group, an alkyl-aryl group of formula -$Q^{10}$-$Ar^{10}$ in which $Q^{10}$ represents a $C_1$ to $C_9$ alkyl residue and $Ar^{10}$ represents a $C_6$ to $C_{14}$ aryl group which is optionally substituted, a polyalkoxy group of formula —$(OCH_2CH_2)_n$—$OR^{15}$ in which n represents an integer between 2 and 5 and $R^{15}$ represents a $C_1$ to $C_{10}$ alkyl group, or a $C_1$ to $C_9$ alkoxy group;

a heteroaryl group which is unsubstituted, or is substituted by a $C_1$ to $C_9$ alkyl group, an optionally substituted $C_6$ to $C_{14}$ aryl group, an alkyl-aryl group of formula -$Q^{11}$-$Ar^{11}$ in which $Q^{11}$ represents a $C_1$ to $C_9$ alkyl residue and $Ar^{11}$ represents a $C_6$ to $C_{14}$ aryl group which is optionally substituted, a polyalkoxy group of formula —$(OCH_2CH_2)_n$—$OR^{15}$ in which n represents an integer between 2 and 5 and $R^{15}$ represents a $C_1$ to $C_{10}$ alkyl group, or a $C_1$ to $C_9$ alkoxy group; or an alkyl-aryl group of formula -$Q^{12}$-$Ar^{12}$ in which $Q^{12}$ represents a $C_1$ to $C_9$ alkyl residue and $Ar^{12}$ represents a $C_6$ to $C_{14}$ aryl group which is optionally substituted.

7. The process as claimed in claim 5, wherein the diol corresponds to the formula (V)

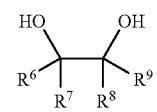

(V)

in which: $R^6$, $R^7$, $R^8$ and $R^9$, which are identical or different, represent:

a hydrogen;

a linear, branched or cyclic $C_1$ to $C_9$ hydrocarbon group which can comprise one or more heteroatoms and which can comprise one or more OH substituents;

a group of formula —$CH_2$—$R^{10}$ in which $R^{10}$ represents a linear, branched or cyclic $C_1$ to $C_9$ hydrocarbon group which can comprise one or more heteroatoms and which can comprise one or more OH substituents;

a group of formula $C(O)OR^{11}$ in which $R^{11}$ represents a hydrogen atom or a $C_1$ to $C_9$ alkyl group;

a $C_5$ to $C_6$ cycloalkyl group which is unsubstituted, or is substituted by a $C_1$ to $C_9$ alkyl group, an optionally substituted $C_6$ to $C_{14}$ aryl group, an alkyl-aryl group of formula -$Q^{13}$-$Ar^{13}$ in which $Q^{13}$ represents a $C_1$ to $C_9$ alkyl residue and $Ar^{13}$ represents a $C_6$ to $C_{14}$ aryl group which is optionally substituted, a polyalkoxy group of formula —$(OCH_2CH_2)_n$—$OR^{15}$ in which n represents an integer between 2 and 5 and $R^{15}$ represents a $C_1$ to $C_{10}$ alkyl group, or a $C_1$ to $C_9$ alkoxy group;

a heteroaryl group which is unsubstituted, or is substituted by a $C_1$ to $C_9$ alkyl group, an optionally substituted $C_6$ to $C_{14}$ aryl group, an alkyl-aryl group of formula -$Q^{14}$-$Ar^{14}$ in which $Q^{14}$ represents a $C_1$ to $C_9$ alkyl residue and $Ar^{14}$ represents a $C_6$ to $C_{14}$ aryl group which is optionally substituted, a polyalkoxy group of formula —(OCH$_2$CH$_2$)$_n$—OR$^{15}$ in which n represents an integer between 2 and 5 and $R^{15}$ represents a $C_1$ to $C_{10}$ alkyl group, or a $C_1$ to $C_9$ alkoxy group;

a $C_6$ to $C_{14}$ aryl group which is unsubstituted, or is substituted by a $C_1$ to $C_9$ alkyl group, an optionally substituted $C_6$ to $C_{14}$ aryl group, an alkyl-aryl group of formula -$Q^{15}$-$Ar^{15}$ in which $Q^{15}$ represents a $C_1$ to $C_9$ alkyl residue and $Ar^{15}$ represents a $C_6$ to $C_{14}$ aryl group which is optionally substituted, a polyalkoxy group of formula —(OCH$_2$CH$_2$)$_n$—OR$^{15}$ in which n represents an integer between 2 and 5 and $R^{15}$ represents a $C_1$ to $C_{10}$ alkyl group, or a $C_1$ to $C_9$ alkoxy radical;

an alkyl-aryl group of formula -$Q^{16}$-$Ar^{16}$ in which $Q^{16}$ represents a $C_1$ to $C_9$ alkyl residue and $Ar^{16}$ represents a $C_6$ to $C_{14}$ aryl group which is optionally substituted;

or $R^6$ and $R^9$ form, together with the carbon atoms carrying them, a double bond; or $R^6$ and $R^9$ form, together with the carbon atoms carrying them, a double bond which is included in an aryl group, formed by $R^7$ and $R^8$ with the two carbon atoms carrying them.

8. The process as claimed in claim 5, wherein the two stages are carried out in just one sequence and with an identical catalytic system.

9. The process of claim 1, wherein the rare earth metal oxide is selected from the group consisting of La$_2$O$_3$, CeO$_2$, Pr$_6$O$_{11}$, Nd$_2$O$_3$, Sm$_2$O$_3$, Y$_2$O$_3$, and mixtures of said rare earth metal oxides thereof.

10. The process as claimed in claim 9, wherein the rare earth metal oxide is La$_2$O$_3$.

11. The process as claimed in claim 9, wherein the rare earth metal oxide is CeO$_2$.

12. The process as claimed of claim 1, wherein the catalytic system is extruded in the form of a monolith.

13. The process of claim 1, carried out at a temperature of between 25° C. and 250° C.

14. The process of claim 1, for which the polyol/alkyl carbonate or polyol/alkylene carbonate molar ratio is between 1/6 and 1/1.

15. The process claim 1, carried out continuously.

16. The process as claimed in claim 2, wherein the compound of formula (I) is a compound of formula (Ia)

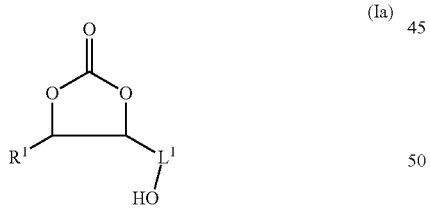

(Ia)

and the polyol of formula (II) is a polyol of formula (IIa)

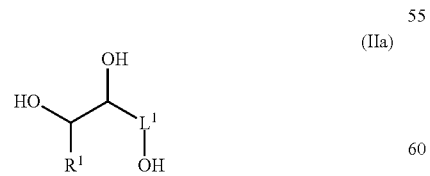

(IIa)

in which $R^1$ represents:
a hydrogen atom;
a linear, branched or cyclic $C_1$ to $C_9$ hydrocarbon group which can comprise one or more heteroatoms and which can comprise one or more OH substituents;

a group of formula —CH$_2$—R$^3$ in which $R^3$ represents a linear or branched $C_1$ to $C_9$ hydrocarbon group which can comprise one or more heteroatoms and which can comprise one or more OH substituents;

an alkyl-aryl group of formula -$Q^1$-Ar in which $Q^1$ represents a $C_1$ to $C_9$ alkyl residue and $Ar^1$ represents a $C_6$ to $C_{14}$ aryl group which is optionally substituted;

a $C_6$ to $C_{14}$ aryl group which is unsubstituted, or is substituted by a $C_1$ to $C_9$ alkyl group, an optionally substituted $C_6$ to $C_{14}$ aryl group, an alkyl-aryl group of formula -$Q^2$-$Ar^2$ in which $Q^2$ represents a $C_1$ to $C_9$ alkyl residue and $Ar^2$ represents a $C_6$ to $C_{14}$ aryl group which is optionally substituted, a polyalkoxy group of formula —(OCH$_2$CH$_2$)$_n$—OR$^{15}$ in which n represents an integer between 2 and 5 and $R^{15}$ represents a $C_1$ to $C_{10}$ alkyl group, or a $C_1$ to $C_9$ alkoxy group;

a heteroaryl group which is unsubstituted, or is substituted by a $C_1$ to $C_9$ alkyl group; a $C_5$ to $C_{14}$ aryl group; an alkyl-aryl group of formula -$Q^3$-$Ar^3$ in which $Q^3$ represents a $C_1$ to $C_9$ alkyl residue and $Ar^3$ represents a $C_6$ to $C_{14}$ aryl group which is optionally substituted, a polyalkoxy group of formula —(OCH$_2$CH$_2$)$_n$—OR$^{15}$ in which n represents an integer between 2 and 5 and $R^{15}$ represents a $C_1$ to $C_{10}$ alkyl group, or a $C_1$ to $C_9$ alkoxy group;

and in which $L^1$ represents:
a linear, branched or cyclic $C_1$ to $C_9$ hydrocarbon group which can comprise one or more heteroatoms and which can comprise one or more OH substituents;

an alkyl-aryl group of formula -$Q^4$-$Ar^4$ in which $Q^4$ represents a $C_1$ to $C_9$ alkyl residue and $Ar^4$ represents a $C_6$ to $C_{14}$ aryl group which is optionally substituted;

a group of formula -$L^2$-CH$_2$ in which $L^2$ represents:
a linear, branched or cyclic $C_1$ to $C_9$ hydrocarbon group which can comprise one or more heteroatoms and which can comprise one or more pendant OH groups;

a $C_5$ to $C_{14}$ aryl group which is unsubstituted, or is substituted by a $C_1$ to $C_9$ alkyl group, an optionally substituted $C_5$ to $C_{14}$ aryl group, an alkyl-aryl group of formula -$Q^5$-$Ar^5$ in which $Q^5$ represents a $C_1$ to $C_9$ alkyl residue and $Ar^5$ represents a $C_6$ to $C_{14}$ aryl group which is optionally substituted, a polyalkoxy group of formula —(OCH$_2$CH$_2$)$_n$—OR$^{15}$ in which n represents an integer between 2 and 5 and $R^{15}$ represents a $C_1$ to $C_{10}$ alkyl group, or a $C_1$ to $C_9$ alkoxy group;

a heteroaryl group which is unsubstituted or is substituted by a $C_1$ to $C_9$ alkyl group, an optionally substituted $C_6$ to $C_{14}$ aryl group, an alkyl-aryl group of formula -$Q^6$-$Ar^6$ in which $Q^6$ represents a $C_1$ to $C_9$ alkyl residue and $Ar^6$ represents a $C_6$ to $C_{14}$ aryl group which is optionally substituted, a polyalkoxy group of formula —(OCH$_2$CH$_2$)$_n$—OR$^{15}$ in which n represents an integer between 2 and 5 and $R^{15}$ represents a $C_1$ to $C_{10}$ alkyl group, or a $C_1$ to $C_9$ alkoxy group;

a $C_6$ to $C_{14}$ aryl group which is unsubstituted, or is substituted by a $C_1$ to $C_9$ alkyl group, an optionally substituted $C_6$ to $C_{14}$ aryl group, an alkyl-aryl group of formula -$Q^5$-$Ar^5$ in which $Q^5$ represents a $C_1$ to $C_9$ alkyl residue and $Ar^5$ represents a $C_6$ to $C_{14}$ aryl group which is optionally substituted, a polyalkoxy group of formula —(OCH$_2$CH$_2$)$_n$—OR$^{15}$ in which n represents an integer between 2 and 5 and $R^{15}$ represents a $C_1$ to $C_{10}$ alkyl group, or a $C_1$ to $C_9$ alkoxy group; or a heteroaryl group which is unsubstituted, or is substituted by a $C_1$ to $C_9$ alkyl group, an optionally substituted $C_6$ to $C_{14}$ aryl group, an alkyl-aryl group of formula -$Q^6$-$Ar^6$ in which $Q^6$ represents a $C_1$ to $C_9$ alkyl residue and $Ar^6$ represents a $C_6$ to $C_{14}$ aryl group which is optionally substituted, a polyalkoxy group of formula $—(OCH_2CH_2)_n—OR^{15}$ in which n represents an integer between 2 and 5 and $R^{15}$ represents a $C_1$ to $C_{10}$ alkyl group, or a $C_1$ to $C_9$ alkoxy group.

17. The process of claim 3, wherein the compound of formula (I) is a compound of formula (Ia)

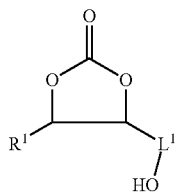

(Ia)

and the polyol of formula (II) is a polyol of formula (IIa)

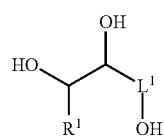

(IIa)

in which $R^1$ represents:
- a hydrogen atom;
- a linear, branched or cyclic $C_1$ to $C_9$ hydrocarbon group which can comprise one or more heteroatoms and which can comprise one or more OH substituents;
- a group of formula $—CH_2—R^3$ in which $R^3$ represents a linear or branched $C_1$ to $C_9$ hydrocarbon group which can comprise one or more heteroatoms and which can comprise one or more OH substituents;
- an alkyl-aryl group of formula $-Q^1-Ar^1$ in which $Q^1$ represents a $C_1$ to $C_9$ alkyl residue and $Ar^1$ represents a $C_6$ to $C_{14}$ aryl group which is optionally substituted;
- a $C_6$ to $C_{14}$ aryl group which is unsubstituted, or is substituted by a $C_1$ to $C_9$ alkyl group, an optionally substituted $C_6$ to $C_{14}$ aryl group, an alkyl-aryl group of formula $-Q^2-Ar^2$ in which $Q^2$ represents a $C_1$ to $C_9$ alkyl residue and $Ar^2$ represents a $C_6$ to $C_{14}$ aryl group which is optionally substituted; a polyalkoxy group of formula $—(OCH_2CH_2)_n—OR^{15}$ in which n represents an integer between 2 and 5 and $R^{15}$ represents a $C_1$ to $C_{10}$ alkyl group, or a $C_1$ to $C_9$ alkoxy group;
- a heteroaryl group which is unsubstituted, or is substituted by a $C_1$ to $C_9$ alkyl group, a $C_5$ to $C_{14}$ aryl group, an alkyl-aryl group of formula $-Q^3-Ar^3$ in which $Q^3$ represents a $C_1$ to $C_9$ alkyl residue and $Ar^3$ represents a $C_6$ to $C_{14}$ aryl group which is optionally substituted, a polyalkoxy group of formula $—(OCH_2CH_2)_n—OR^{15}$ in which n represents an integer between 2 and 5 and $R^{15}$ represents a $C_1$ to $C_{10}$ alkyl group, or a $C_1$ to $C_9$ alkoxy group;

and in which $L^1$ represents:
- a linear, branched or cyclic $C_1$ to $C_9$ hydrocarbon group which can comprise one or more heteroatoms and which can comprise one or more OH substituents;
- an alkyl-aryl group of formula $-Q^4-Ar^4$ in which $Q^4$ represents a $C_1$ to $C_9$ alkyl residue and $Ar^4$ represents a $C_6$ to $C_{14}$ aryl group which is optionally substituted;
- a group of formula $-L^2-CH_2$ in which $L^2$ represents:
  - a linear, branched or cyclic $C_1$ to $C_9$ hydrocarbon group which can comprise one or more heteroatoms and which can comprise one or more pendant OH groups;
  - a $C_5$ to $C_{14}$ aryl group which is unsubstituted, or is substituted by a $C_1$ to $C_9$ alkyl group, an optionally substituted $C_5$ to $C_{14}$ aryl group, an alkyl-aryl group of formula $-Q^5-Ar^5$ in which $Q^5$ represents a $C_1$ to $C_9$ alkyl residue and $Ar^5$ represents a $C_6$ to $C_{14}$ aryl group which is optionally substituted, a polyalkoxy group of formula $—(OCH_2CH_2)_n—OR^{15}$ in which n represents an integer between 2 and 5 and $R^{15}$ represents a $C_1$ to $C_{10}$ alkyl group, or a $C_1$ to $C_9$ alkoxy group;
  - a heteroaryl group which is unsubstituted, or is substituted by a $C_1$ to $C_9$ alkyl group, an optionally substituted $C_6$ to $C_{14}$ aryl group, an alkyl-aryl group of formula $-Q^6-Ar^6$ in which $Q^6$ represents a $C_1$ to $C_9$ alkyl residue and $Ar^6$ represents a $C_6$ to $C_{14}$ aryl group which is optionally substituted, a polyalkoxy group of formula $—(OCH_2CH_2)_n—OR^{15}$ in which n represents an integer between 2 and 5 and $R^{15}$ represents a $C_1$ to $C_{10}$ alkyl group, or a $C_1$ to $C_9$ alkoxy group;
- a $C_6$ to $C_{14}$ aryl group which is unsubstituted, or is substituted by a $C_1$ to $C_9$ alkyl group, an optionally substituted $C_6$ to $C_{14}$ aryl group, an alkyl-aryl group of formula $-Q^5-Ar^5$ in which $Q^5$ represents a $C_1$ to $C_9$ alkyl residue and $Ar^5$ represents a $C_6$ to $C_{14}$ aryl group which is optionally substituted, a polyalkoxy group of formula $—(OCH_2CH_2)_n—OR^{15}$ in which n represents an integer between 2 and 5 and $R^{15}$ represents a $C_1$ to $C_{10}$ alkyl group, or a $C_1$ to $C_9$ alkoxy group; or
- a heteroaryl group which is unsubstituted, or is substituted by a $C_1$ to $C_9$ alkyl group, an optionally substituted $C_6$ to $C_{14}$ aryl group, an alkyl-aryl group of formula $-Q^6-Ar^6$ in which $Q^6$ represents a $C_1$ to $C_9$ alkyl residue and $Ar^6$ represents a $C_6$ to $C_{14}$ aryl group which is optionally substituted, a polyalkoxy group of formula $—(OCH_2CH_2)_n—OR^{15}$ in which n represents an integer between 2 and 5 and $R^{15}$ represents a $C_1$ to $C_{10}$ alkyl group, or a $C_1$ to $C_9$ alkoxy group.

18. The process of claim 1, wherein the process is carried out in the presence of the less than 5% of water.

* * * * *